United States Patent [19]
Bambury et al.

[11] 3,989,687
[45] Nov. 2, 1976

[54] 4-OXO-1-PYRIDINYL PENICILLIN DERIVATIVES

[75] Inventors: Ronald E. Bambury; Michael L. Edwards, both of Cincinnati; Laird F. Miller, Loveland, all of Ohio

[73] Assignee: Richardson-Merrell Inc., Wilton, Conn.

[22] Filed: Oct. 9, 1975

[21] Appl. No.: 621,208

Related U.S. Application Data

[60] Division of Ser. No. 508,999, Sept. 27, 1974, which is a continuation-in-part of Ser. No. 413,565, Nov. 7, 1973, abandoned.

[52] U.S. Cl. .......................... 260/239.1; 260/243 C; 424/246; 424/271
[51] Int. Cl.² ..................................... C07D 499/58
[58] Field of Search ................................ 260/239.1

[56] References Cited
UNITED STATES PATENTS

| 3,652,547 | 3/1972 | Wolf et al. | 260/239.1 |
| 3,873,523 | 3/1975 | Doub et al. | 260/239.1 |
| 3,929,782 | 12/1975 | Breuer | 260/239.1 |
| 3,953,428 | 4/1976 | Murakami et al. | 260/239.1 |

FOREIGN PATENTS OR APPLICATIONS

| 2,345,402 | 3/1975 | Germany | 260/239.1 |

Primary Examiner—Gerald A. Schwartz
Attorney, Agent, or Firm—William J. Stein; Eugene O. Retter; George W. Rauchfuss, Jr.

[57] ABSTRACT

Novel substituted(4-oxo-1-pyridinyl)acetylamino-penicillin and cephalosporin derivatives are prepared which are useful antibacterial agents.

6 Claims, No Drawings

4-OXO-1-PYRIDINYL PENICILLIN DERIVATIVES

CROSS-REFERENCES

This is a division of application Ser. No. 508,999, filed Sept. 27, 1974, which is a continuation-in-part of application Ser. No. 413,565, filed Nov. 7, 1973, now abandoned.

FIELD OF THE INVENTION

This invention relates to novel derivatives of substituted(4-oxo-1-pyridinyl)acetylamino-penicillin and cephalosporins, to their methods of preparation, and to their usefulness as antibacterial agents.

BACKGROUND OF THE INVENTION

This invention relates to new synthetic compounds of the penicillin and cephalosporin classes which are useful as antibacterial agents. These compounds possess a high degree of activity against a large number of microorganisms. The cephalosporin derivatives of this invention are particularly useful against penicillinase-producing microorganisms. As antibacterial agents the compounds of this invention are therapeutically effective in the treatment of infectious diseases due to gram-positive and gram-negative bacteria in poultry and animals, incuding man. In addition, the compounds of this invention are useful as animal feed supplements and as the active ingredient in germicidal preparations employed as surface disinfectants.

PRIOR ART

The cleavage of penicillins to 6-aminopenicillanic acid in 1959 and the chemical cleavage of cephalosporin to give the corresponding 7-aminocephalosporanic acid made possible the synthesis of new synthetic penicillins and cephalosporins not previously available via fermentation procedures. Acylation of the amino group has produced derivatives containing a heterocyclic ring in the 6-position side chain, as in the case of the penicillin series, or in the corresponding 7-position side chain, as in the case of the cephalosporin series. Such heterocycles include the thiophene ring, as for example, U.S. Pat. Nos. 3,218,318, 3,449,338 and 3,498,979 (cephaloridine and cephalothin); picoline, U.S. Pat. No. 3,553,203; hydantoin, U.S. Pat. No. 3,227,712; and various other nitrogen containing heterocycles including pyrrolidine and nicotinic acid, U.S. Pat. No. 3,308,120.

In each instance the heterocyclic moity is attached to a side chain, generally that of an acetyl radical, via one of the ring carbon atoms. The present invention is concerned with 4-oxo-1-pyridinyl derivatives which are linked directly to the acetyl radical through the hetero atom. Examples known to applicants containing this type of linkage, and in this regard representing the closest piror art, are the tetrazole ring in U.S. Pat. No. 3,516,997 (cefazolin) and certain quinazolinyl derivatives of penicillanic acid, U.S. Pat. No. 3,652,547.

SUMMARY OF THE INVENTION

This invention relates to novel 4-oxo-1-pyridinyl penicillin and cephalosporin derivatives. More particularly, this invention relates to substituted(4-oxo-1-pyridinyl)acetylamino-penicillin and cephalosporin derivatives which are useful as antibacterial agents and which may be represented by the general formula:

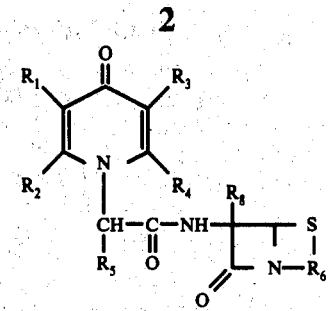

wherein
$R_1$, $R_2$, $R_3$ and $R_4$ are each selected from the group consisting of hydrogen, halogen, hydroxyl, lower alkyl, trifluoromethyl, nitro, amino, cyano, carboxy, carbomethoxy, carbethoxy and when $R_1$ is taken in combination with $R_2$ forms the cyclic radical $-CH_2CH_2CH_2CH_2-$ and $-CH=CH-CH=CH-$;

$R_5$ is selected from the group consisting of hydrogen, methyl, carboxy, carbomethoxy and carbethoxy;

$R_6$ is selected from the group

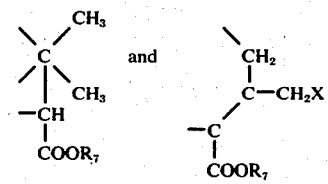

X is selected from the group consisting of hydrogen, hydroxy, acetoxy, N-pyridinium, 5-methyl-1,3,4-thiadiazol-2-ylthio and 1-methyl-1,2,3,4-tetrazol-5-ylthio;

$R_7$ is selected from the group consisting of hydrogen, alkanoyloxymethyl, alkanoylaminomethyl, alkoxycarbonylaminomethyl and p-(alkanoyloxy)benzyl in which the alkanoyl or alkoxy group contains from 1 to 5 carbon atoms;

$R_8$ is hydrogen or methoxy; and
the pharmaceutically acceptable salts thereof.

The compounds of the present invention are prepared by the condensation of a 6-aminopenicillanic acid or a 7-aminocephalosporanic acid with a (substituted)4-oxo-1-pyridinylacetic acid as illustrated in the following reaction scheme.

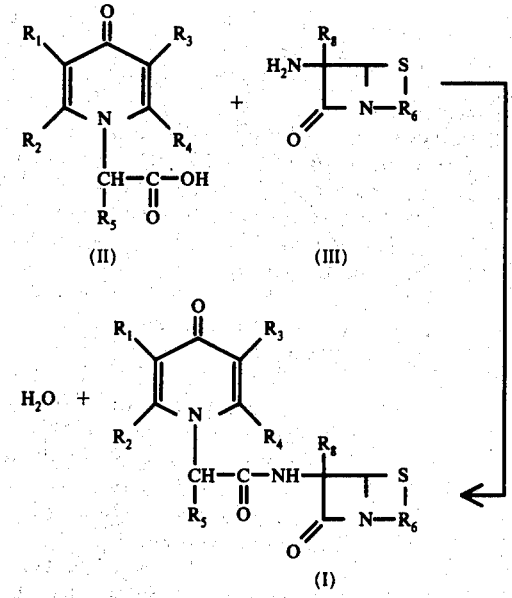

DETAILED DESCRIPTION OF THE INVENTION

All of the compounds of the present invention contain a 4-oxo-1-pyridinyl radical or a 4-pyridone moiety at the terminal position of the acetylamino side chain, as indicated in general Formula (I) above. In the case of the penicillin series, the acetylamino side chain is enumerated as the 6-position, whereas in the cephalosporin series of compounds the 7-position is enumerated. The numbering system for these two series of compounds is illustrated for the inermediates 6-aminopenicillanic acid (IV) and 7-aminocephalosporanic acid (V) below:

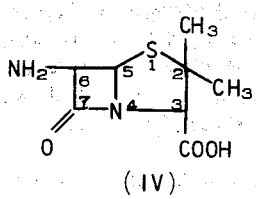

(IV)

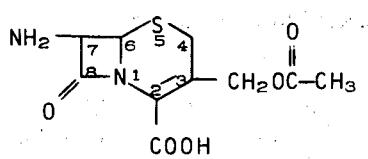

(V)

The 4-pyridone moiety attached to the acetylamino side chain may be substituted or unsubstituted. These substituents are present in either the 2-, 3-, 5- or 6-positions of the pyridine nucleus and include the following radicals: halogen, hydroxyl, lower alkyl, trifluoromethyl, nitro, amino, cyano, carboxyl and the methyl and ethyl esters of the carboxyl radical. The term halogen includes the fluoro, chloro, bromo and iodo radicals. The term lower alkyl as used herein includes both straight and branched chain aliphatic hydrocarbon radicals having from 1 to 4 carbon atoms. Specifically included are such members as methyl, ethyl, propyl, isopropyl, butyl, isobutyl, and the t-butyl radicals.

In addition to the various substituents described above, the 4-pyridone moiety can be considered as substituted with an adjacent saturated or unsaturated six-membered ring. Thus, the symbol $R_1$ when taken in combination with the adjacent symbol $R_2$ can be viewed as forming an attached 6-membered alicyclic or aromatic derivative at the 2,3-position of the pyridine ring. These derivatives are more properly termed 2-[substituted(4-oxo-1-tetrahydroquinolinyl)-]acetylamino and 2-[substituted(4-oxo-1-quinolinyl)-]acetylamino derivatives of penicillins and cephalosporins. Due to the symmetry of the pyridine molecule only one pair of adjacent symbols need be so defined. The present invention is not intended to include the tricyclic heterocyclic dibenzo-pyridine or acridine ring systems.

In addition to the mandatory substitution of the 2-methyl group of the acetylamino or acetamido portion of the molecule with 4-oxo-1-pyridinyl radical, the 2-methyl group may contain additional substitution in the form of a methyl radical or a carboxyl radical as represented by the symbol $R_5$. When $R_5$ is methyl, the compounds are more properly termed as propionyl derivatives of 6-aminopenicillanic acid or of 7-aminocephalosporanic acid. However, for the sake of uniformity in nomenclature, they are termed as 2-(substituted)acetylamino derivatives herein. Thus, for example, in the case of a cephalosporanic acid derivative in which $R_5$ is methyl and the 4-pyridone remains unsubstituted, the compound is designated as 7-[2-(4-oxo-1-pyridyl)-2-methylacetylamino]cephalosporanic acid. In addition to the carboxyl radical at $R_5$ the methyl and ethyl esters or carbomethoxy and carbethoxy radicals are also contemplated to be within the scope of the present invention.

This invention is essentially concerned with the preparation and description of 2-(4-oxo-1-pyridinyl-)acetylamino side-chain derivatives of the β-lactam antibiotics. These derivatives are prepared by condensation with the readily available 6-amino penicillanic acid or any of the available 7-aminocephalosporin intermediates. Thus, where $R_6$ is the radical

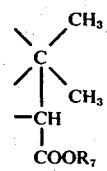

derivaties of the penicillin series are delineated, whereas when $R_6$ is the radical

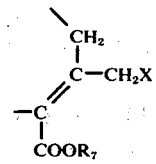

derivatives of the cephalosporin series are described.

The β-lactam nucleus can remain unsubstituted or it can be substituted with a methoxy substutuent as indicated by the symbol $R_8$. Such substitution occurs at the 6-position of the penicillin series and at the 7-position of the cephalosporin series of compounds.

Both the 3-position of the penicillin and the 2-position of the cephalosporin series of compounds are substituted by a carboxylic acid or a carboxylic acid ester as represented by the partial structure —COOR$_7$. When $R_7$ is hydrogen, the corresponding penicillanic acids or cephalosporanic acids are obtained. Additionally, the symbol $R_7$ can represent the following radicals: alkanoyloxymethyl, alkanoylaminomethyl, alkoxycarbonylaminomethyl and p-(alkanoyloxy)benzyl. These esters confer excellent properties of absorption upon the molecule and at the same time are physiologically labile. Thus, these esters are readily absorbed from the gastro-intestinal tract and enzymatically hydrolyzed to the corresponding penicillanic or cephalosporanic acids thereby, providing excellent oral activity.

Certain specific variations within the cephalosporin series are further indicated by the symbol X. Thus, where X is hydrogen the desacetoxycephalosporanic acids are delineated; and where the symbol X is hydroxyl, the desacetylcephalosporanic acids are indicated. Where the symbol X represents an acetoxy radical the β-lactam nucleus is that of cephalosporanic acid. Additional substituents at the 3-position of decephalosporanic acid which are included within the purview of the present invention and represented by the symbol X are the N-pyridinium, the 5-methyl-1,3,4-thiadiazol-2-ylthio and the 1-methyl-1,2,3,4-tetrazol-5-ylthio radicals.

The pharmaceutically acceptable salts of the compounds of Formula (I) above include the non-toxic, carboxylic acid salts formed with any suitable inorganic or organic bases. Illustratively, these salts include those of alkali metals, as for example, sodium and potassium; alkaline earth metals, such as calcium and magnesium; light metals of Group III a including aluminum; and organic primary, secondary and tertiary amines, as for example, trialkylamines, including triethylamine, procaine, dibenzylamine, vinylamine, N,N'-dibenzylethylenediamine, dihydroabietylamine, N-(lower)alkylpiperidine, and additional amines which have been used to form non-toxic salts with benzylpenicillin. These salts can be prepared using conventional means such as contacting and neutralizing a solution of the carboxylic acid in a polar solvent with a stoichiometric quantity of a base.

Also included as pharmaceutically acceptable acid addition salts are the non-toxic organic or inorganic acid addition salts of the base compounds of Formula (I) above. Illustrative inorganic acids which form suitable salts include hydrochloric, hydrobromic, sulfuric and phosphoric acids as well as acid metal salts such as sodium monohydrogen orthophosphate and potassium hydrogen sulfate. Illustrative organic acids which form suitable salts include mono, di and tricarboxylic acids, as for example, acetic, glycolic, lactic, pyruvic, malonic, succinic, glutaric, fumaric, malic, tartaric, citric, ascorbic, maleic, hydroxymaleic, benzoic, p-hydroxybenzoic, phenylacetic, cinnamic, salicylic, 2-phenoxybenzoic and sulfonic acids such as methane sulfonic acid and 2-hydroxyethane sulfonic acid. Such salts can exist in either a hydrated or a substantially anhydrous form.

In addition to the non-toxic, carboxylic acid salts and the non-toxic acid addition salts of the base compounds, the term pharmaceutically acceptable salts is taken to include internal salts or zwitter-ions of those compounds of Formula (I) above which are amphoteric in nature. Thus, compounds such as 7-[2-(4-oxo-1-pyridinium)acetylamino]cephalosporanate, 7-[2-(4-oxo-1-pyridinium)acetylamino]-3-[(5-methyl-1,3,4-thiadiazole-2-ylthio)methyl]decephalosporanate or 7-[2-(4-oxo-1-pyridinyl)acetylamino](pyridiniummethyl)decephalosporanate, can exist as a dipolar ion, particularly when they are in solution.

Illustrative specific base compounds which are encompassed by Formula (I) above include:

6-[2-(4-oxo-1-pyridinyl)acetylamino]penicillanic acid,
6-[2-(2-hydroxy-4-oxo-1-pyridinyl)acetylamino]penicillanic acid,
6-[2-(3-trifluoromethyl-4-oxo-1-pyridinyl)-2-methylacetylamino]penicillanic acid,
6-[2-(2,3,5-trichloro-4-oxo-1-pyridinyl)acetylamino]penicillanic acid,
6-[2-(3-cyano-4-oxo-1-pyridinyl)acetylamino]penicillanic acid,
6-[2-(2-ethyl-5-methyl-4-oxo-1-pyridinyl)-2-carbethoxyacetylamino]penicillanic acid,
6-[2-(2-amino-4-oxo-1-quinolinyl)acetylamino]penicillanic acid, acetoxymethyl 6-[2-(4-oxo-1-pyridinyl)acetylamino]penicillanate,
N-acetylaminomethyl 6-[2-(3-chloro-4-oxo-1-pyridinyl) acetylamino]penicillanate,
(N-ethoxycarbonyl-N-methyl)aminomethyl 6-[2-(2-chloro-4-oxo-1-quinolinyl)acetylamino]penicillanate,
7-[2-(4-oxo-1-pyridinyl)acetylamino]cephalosporanic acid,
7-[2-(2-nitro-4-oxo-1-pyridinyl)acetylamino]cephalosporanic acid,
7-[2-(2,5-dicarboxy-4-oxo-1-pyridinyl)-2-carboxyacetylamino]cephalosporanic acid,
7-[2-(2-chloro-3-hydroxy-4-oxo-1-tetrahydroquinolinyl)acetylamino]cephalosporanic acid,
7-[2-(2,3,5,6-tetramethyl-4-oxo-1-pyridinyl)-2-methylacetylamino]cephalosporanic acid,
7-[2-(2,5-dicarbethoxy-4-oxo-1-pyridinyl)-2-carbethoxyacetylamino]cephalosporanic acid,
pivaloyloxymethyl 7-[2-(4-oxo-1-pyridinyl)acetylamino]cephalosporanate,
p-acetyloxybenzyl 7-[2-(3,5-dicyano-4-oxo-1-pyridinyl)acetylamino]cephalosporanate,
(N-propionyl-N-methyl)aminomethyl 7-[2-(3-amino-4-oxo-1-pyridinyl)-2-carbethoxyacetylamino]cephalosporanate,
7-[2-(3,5-dimethyl-4-oxo-1-pyridinyl)-2-methylacetylamino]desacetoxycephalosporanic acid,
7-[2-(2-cyano-4-oxo-1-quinolinyl)acetylamino]-desacetoxycephalosporanic acid,
7-[2-(2,3,5,6-tetraiodo-4-oxo-1-pyridinyl)acetylamino]desacetoxycephalosporanic acid,
7-[2-(2,6-dihydroxy-4-oxo-1-pyridinyl)-2-carbomethoxyacetylamino]desacetoxycephalosporanic acid,
7-[2-(2,6-dinitro-4-oxo-1-pyridinyl)acetylamino]-desacetoxycephalosporanic acid,
7-[2-(4-oxo-1-pyridinyl)acetylamino]desacetylcephalosporanic acid,
7-[2-(2-carboxy-5-methyl-4-oxo-1-pyridinyl)-2-carboxyacetylamino]desacetylcephalosporanic acid,
7-[2-(3-amino-5-bromo-4-oxo-1-pyridinyl)acetylamino]desacetylcephalosporanic acid,
7-[2-(3-carbomethoxy-4-oxo-1-tetrahydroquinolinyl)-2-methylacetylamino]desacetylcephalosporanic acid,
7-[2-(3-trifluoromethyl-4-oxo-1-pyridinyl)acetylamino]desacetylcephalosporanic acid,
7-[2-(5-chloro-2-cyano-4-oxo-1-pyridinyl)acetylamino]desacetylcephalosporanic acid,
p-propionyloxybenzyl 7-[2-(3,5-dichloro-4-oxo-1-pyridinyl)-2-carbomethoxyacetylamino]desacetylcephalosporanate,
isopropoxymethyl 7-[2-(5-nitro-4-oxo-1-quinolinyl)acetylamino]desacetylcephalosporanate,
pivaloyloxymethyl 7-[2-(4-oxo-1-tetrahydroquinolinyl)acetylamino]desacetoxycephalosporanate,
7-[2-(4-oxo-1-pyridinyl)acetylamino]-3-(pyridiniummethyl)decephalosporanate,
7-[2-(2-hydroxy-3,5-dibromo-4-oxo-1-pyridinyl)acetylamino]-3-(pyridiniummethyl)decephalosporanate,
7-[2-(2,6-dicyano-4-oxo-1-pyridinyl)acetylamino]-3-(pyridiniummethyl)decephalosporanate,
7-[2-(2-carbomethoxy-4-oxo-1-pyridinyl)-2-carbethoxyacetylamino]-3-(pyridiniummethyl)decephalosporanate,
7-[2-(4-oxo-1-quinolinyl)acetylamino]-3-pyridiniummethyl)decephalosporanate,
7-[2-(3-chloro-2,6-dimethyl-4-oxo-1-pyridinyl)-2-methylacetylamino]-3-(pyridiniummethyl)decephalosporanate,
7-[2-(4-oxo-1-pyridinyl)acetylamino]-3-[(5-methyl-1,3,4-thiadiazol-2-ylthio)methyl]decephalosporanic acid, 7-[2-(2-bromo-3,5-dichloro-4-oxo-1-pyridinyl)acetylamino]-3-[(5-methyl-1,3,4-thiadiazol-2-ylthio)methyl]decephalosporanic acid, 7-[2-(4-oxo-1-tetrahydroquinolinyl)-2-carboxyacetylamino]-3-[(5-methyl-1,3,4-thiadiazol-2-ylthio)methyl]decephalosporanic acid, 7-[2-(3-cyano-4-oxo-1-pyridinyl)-2-methylacetylamino]-3-[(5-methyl-1,3,4-thiadiazol-2-ylthio)methyl]decephalosporanic acid, 7-[2-(3,5-dihydroxy-4-oxo-1-pyridinyl)acetylamino]-3-[(5-methyl-1,3,4-thiadiazol-2-ylthio)methyl]decephalosporanic acid, pivaloxymethyl 7-[2-(4-oxo-1-pyridinyl)acetylamino]-3-[(5-methyl-1,3,4-thiadiazol-2-ylthio)methyl]decephalosporanate, (N-ethoxycarbonyl-N-methyl)aminomethyl 7-[2-(5-chloro-4-oxo-1-tetrahydroquinolinyl)-2-methylacetylamino]-3-[(5-methyl-1,3,4-thiadiazol-2-ylthio)methyl]decephalosporanate, (N-acetyl-N-methyl)aminomethyl 7-[2-(3-cyano-4-oxo-1-pyridinyl)acetylamino]-3-[(5-methyl-1,3,4-thiadiazol-2-ylthio)methyl]decephalosporanate, 7-[2-(4-oxo-1-pyridinyl)acetylamino]-3-[(1-methyl-1,2,3,4-tetrazol-5-ylthio)methyl]decephalosporanic acid, 7-[2-(5-methyl-2-propyl-4-oxo-1-pyridinyl)-2-methylacetylamino]-3-[(1-methyl-1,2,3,4-tetrazol-5-ylthio)methyl]decephalosporanic acid, 7-[2-(3-trifluoromethyl-4-oxo-1-pyridinyl)acetylamino]-3-[(1-methyl-1,2,3,4-tetrazol-5-ylthio)methyl]decephalosporanic acid, 7-[2-(4-oxo-1-quinolinyl)-2-carboxyacetylamino]-3-[(1-methyl-1,2,3,4-tetrazol-5-ylthio)methyl]decephalosporanic acid, 7-[2-(2-chloro-5,6-difluoro-4-oxo-1-pyridinyl)acetylamino]-3-[(1-methyl-1,2,3,4-tetrazol-5-ylthio)methyl]decephalosporanic acid, acetoxymethyl 7-[2-(4-oxo-1-pyridinyl)acetylamino]-3-[(1-methyl-1,2,3,4-tetrazol-5-ylthio)methyl]decephalosporanate, (N-methoxycarbonyl-N-methyl)aminomethyl 7-[2-(2,6-dihydroxy-4-oxo-1-pyridinyl)-2-carbethoxyacetylamino]-3-[(1-methyl-1,2,3,4-tetrazol-5-ylthio)methyl]decephalosporanate, p-pivaloyloxybenzyl 7-[2-(5-trifluoromethyl-4-oxo-1-quinolinyl)acetylamino]-3-[(1-methyl-1,2,3,4-tetrazol-5-ylthio)methyl]decephalosporanate, 7-methoxy-7-[2-(4-oxo-1-pyridinyl)acetylamino]cephalosporanic acid, 7-methoxy-7-[2-(4-oxo-1-pyridinyl)acetylamino]-3-[(5-methyl-1,3,4-thiadiazol-2-ylthio)methyl]decephalosporanic acid, 6-methoxy-6-[2-(4-oxo-1-pyridinyl)acetylamino]penicillanic acid, 7-methoxy-7-[2-(4-oxo-1-pyridinyl)acetylamino]decephalosporanic acid, 6-methoxy-6-[2-(3,5-dicyano-4-oxo-1-pyridinyl)acetylamino]penicillanic acid, 6-methoxy-6-[2-(5-nitro-4-oxo-1-quinolinyl)-2-carbethoxyacetylamino]penicillanic acid, pivaloyloxymethyl 6-methoxy-6-[2-(4-oxo-1-pyridinyl)acetylamino]penicillanate, 7-methoxy-7-[2-(5-chloro-4-oxo-1-quinolinyl)-2-methylacetylamino]cephalosporanic acid, 7-methoxy-7-[2-(2-hydroxy-4-oxo-1-pyridinyl)-2-carbomethoxyacetylamino]cephalosporanic acid, acetoxymethyl 7-methoxy-7-[2-(4-oxo-1-pyridinyl)acetylamino]cephalosporanate, N-acetylaminomethyl 7-methoxy-7-[2-(2,6-dimethyl-4-oxo-1-pyridinyl)-2-carbethoxyacetylamino]cephalosporanate, 7-methoxy-7-[2-(4-oxo-1-pyridinyl)acetylamino]desacetylcephalosporanic acid, p-acetoxybenzyl 7-methoxy-7-[2-(5-trifluoromethyl-4-oxo-1-quinolinyl)-2-ethylacetylamino]desacetoxycephalosporanate, acetoxymethyl 7-methoxy-7-[2-(4-oxo-1-pyridinyl)acetylamino]-3-[(5-methyl-1,3,4-thiadiazol-2-ylthio)methyl]decephalosporanate, (N-ethoxycarbonyl-N-methyl)aminomethyl 7-methoxy-7-[2-(4-oxo-1-pyridinyl)acetylamino]-3-[(1-methyl-1,2,3,4-tetrazol-5-ylthio)methyl]decephalosporanate, pivaloyloxymethyl 7-methoxy-7-[2-(4-oxo-1-pyridinyl)acetylamino]-3-[(1-methyl-1,2,3,4-tetrazol-5-ylthio)methyl]decephalosporanate.

The products of the present invention are prepared by reacting a β-lactam 6-aminopenicillanic acid or 7-aminocephalosporanic acid, or derivative thereof, having the formula

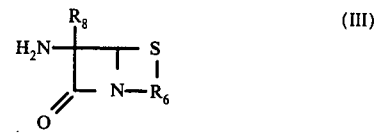
(III)

with a 4-oxo-1-pyridinylacetic acid having the formula

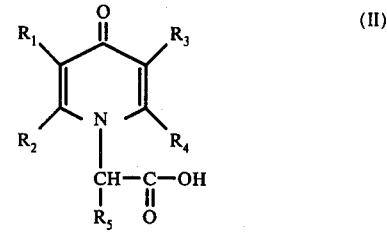
(II)

wherein the symbols $R_1$, $R_2$, $R_3$, $R_4$, $R_5$, $R_6$ and $R_8$ have the values previously assigned.

The β-lactam starting materials (III) are all known compounds. The compound, 6-aminopenicillanic acid, having the formula

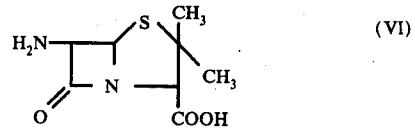
(VI)

can be prepared using biological methods and can also be prepared by the hydrolysis of various penicillins as described in U.S. Pat. No. 3,499,909.

Hydrolysis of the antibiotic cephalosporin C results in the formation of 7-aminocephalosporanic acid, Loder et al., Biochem. J. 79, 408–416 (1961), having the formula

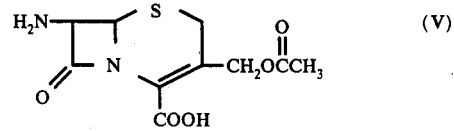
(V)

The compound 7-aminodesacetoxycephalosporanic acid having the formula

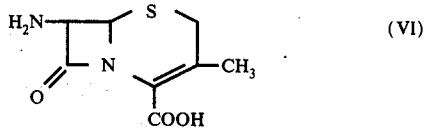
(VI)

is prepared by the catalytic reduction of the cephalosporin C, followed by the hydrolytic removal of the 5-aminoadipoyl side chain as described in U.S. Pat. No. 3,129,224.

Those compounds of the β-lactam starting material (III) above wherein the symbol $R_8$ represents a methoxy group have been previously described in U.S. Pat. No. 3,778,432.

Treatment of cephalosporin C with an acetyl esterase prepared from orange peel, Jeffery et al., Biochem. J., 81, 591 (1961) results in the formation of 3-hydroxymethyl-7-aminodecephalosporanic acid or 7-aminodesacetylcephalosporanic acid having the formula

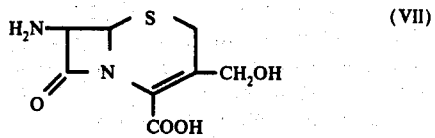

(VII)

Treatment of cephalosporin C with pyridine followed by an acid hydrolysis produces the compound, 7-amino-3-(pyridiniummethyl)decephalosporanic acid having the formula shown below. The preparation of this compound is known in the art and described, for example, in U.S. Pat. No. 3,117,126 and British Pat. Nos. 932,644, 957,570 and 959,054.

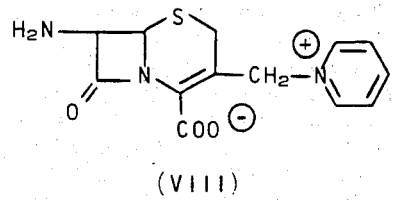

(VIII)

The 3-thiolated 7-aminocephalosporanic acids can be obtained by reacting 7-aminocephalosporanic acid with the appropriate thiol as described in U.S. Pat. No. 3,516,997. Thus when 5-methyl-1,3,4-thiadiazole-2-thiol is employed the compound 7-amino-3-[(5-methyl-1,3,4-thiadiazol-2-ylthio)methyl]decephalosporanic acid is obtained, which has the formula

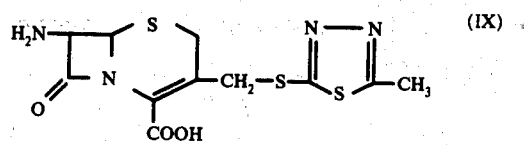

(IX)

When the compound 1-methyl-1,2,3,4-tetrazole-5-thiol is employed the compound 7-amino-3-[(1-methyl-1,2,3,4-tetrazol-5-ylthio)methyl]decephalosporanic acid is obtained having the formula

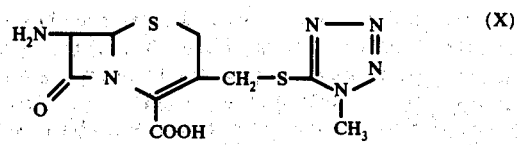

(X)

The 4-oxo-1-pyridinyl-(substituted)-acetic acids (II) used as starting materials are for the most part known compounds which can be synthesized in either one or two steps via the condensation of an alkali metal salt of an hydroxypyridine (XI) with ethylbromoacetate or a substituted ethylbromoacetate (XII). Generally the potassium salt of hydroxypyridine is preferred to effect condensation, and the resulting ester hydrolyzed to the desired 4-oxo-1-pyridinyl-(substituted)-acetic acid (II) with an aqueous base as illustrated in the following reaction scheme:

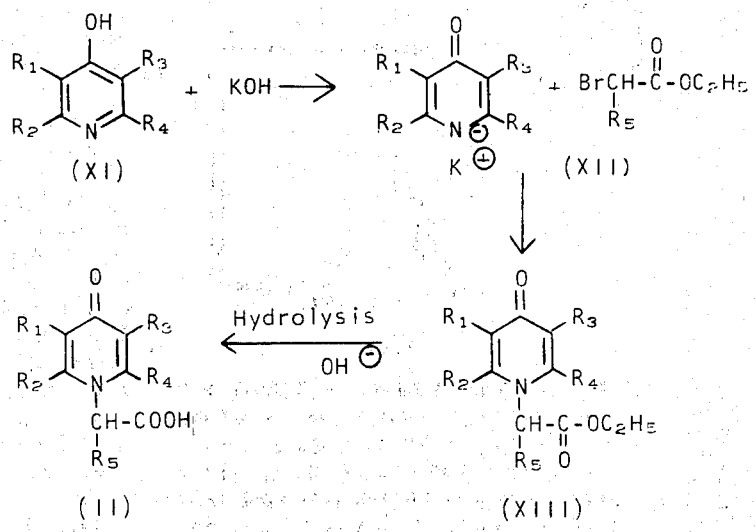

Alternatively, the 4-oxo-1-pyridinyl-(substituted)acetic acids (II) are directly prepared by reaction of a 2-pyridone with chloroacetic acid or a substituted chloroacetic acid (XIV) in the presence of a strong aqueous base as indicated in the following reaction scheme:

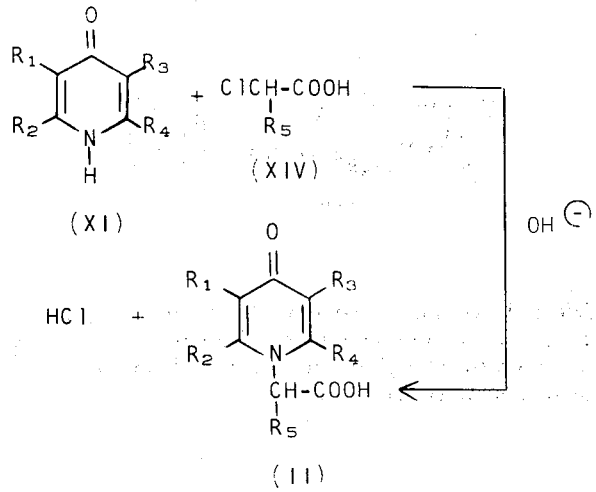

A preferred method involves the prior silylation of a (substituted)-4-hydroxypyridine (XI) in the presence of an organic base, such as triethylamine, with a tri-(lower alkyl) substituted halosilane, as for example, chlorotrimethylsilane. This method enables purification of the silylated intermediate which, in turn, results in the preparation of (substituted)-4-oxo-1-pyridinylacetic acids (II) having fewer contaminants and in an increased yield.

The (substituted)-4-oxo-1-pyridinyl acetic acids of Formula (II) wherein $R_5$ is hydrogen can also be prepared by treating pyrone or by treating a substituted pyrone with glycine in the presence of a base. In this nucleophilic reaction the pyrone ring is opened, water eliminated and the ring reclosed with the amino nitrogen atom now contained in the pyridine ring. This reaction, which is generally conducted at elevated temperatures for an extended period of time, can be illustrated as follows using 2,6-dimethyl-4-pyrone (XV) to prepare 2,6-dimethyl-4-pyridone-1-acetic acid (XVI).

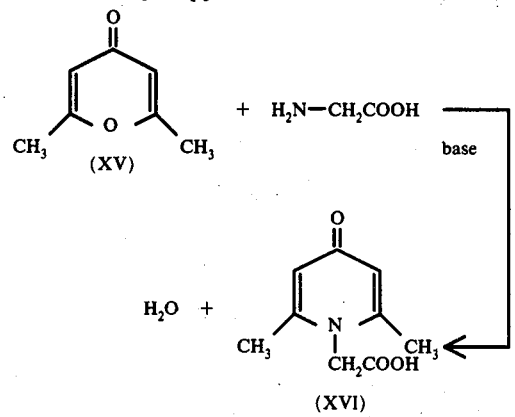

In general the 6-aminopenicillanic or 7-aminocephalosporanic acid derivatives of the present invention can be prepared by the condensation of a 4-oxo-1-pyridinylacetic acid (II) and an amino-$\beta$-lactam (III) as previously indicated. The coupling reaction is generally conducted in solution in the presence of a suitable solvent. Suitable solvents include acetone, dioxane, acetonitrile, chloroform, ethylene chloride, tetrahydrofuran or other inert and readily available solvents. The coupling reaction is further generally conducted in the presence of a base, such as an alkali metal carbonate or an alkali metal acid carbonate, trialkylamine, in which the alkyl group has from 1 to 5 carbon atoms or pyridine. The temperature of the coupling reaction can vary from $-20°$ C. to $100°$ C. with the preferred temperature at room temperature or slightly below room temperature. The reaction time can vary anywhere from 15 minutes to as long as 36 hours, depending, of course, upon the temperature of the reaction mixture and the reactivity of the particular reactants employed. Preferably a period of from 1 to 8 hours is employed. Following the condensation reaction, the reaction products are isolated and recovered using conventional extraction and crystallization procedures which are well known to those skilled in the art.

In order to provide a suitable driving force for the coupling reaction a coupling agent is employed. One type of coupling agent acts essentially as a dehydration agent, promoting the acylation and removing the water formed during the reaction. Such dehydrative coupling agents or dehydration agents, as termed herein, include the compounds: dicyclohexylcarbodiimide, N-cyclohexyl-N-morpholinomethylcarbodiimide, pentamethylketone-N-cyclohexylimine, N-ethyl-5-phenylisoxazolium-3-sulfonate and phosphorous trichloride. The compound dicyclohexylcarbodiimide represents a preferred dehydration agent particularly in the preparation of the cephalosporin series of compounds.

A second class of coupling agents can be viewed as interacting with the various 4-oxo-1-pyridinyl acetic acids employed in such a manner as to activate the carbonyl radical of the acetic acid portion of the molecule, thereby forming a reactive intermediate. This reactive intermediate, in turn, acylates the amino-$\beta$-lactam. Thus, the corresponding acid halides, acid azides, mixed acid anhydrides with alkylphosphoric acid or alkylcarbonic acid, acid amides with amidazole or a 4-substituted imidazole, acid cyanomethyl esters and acid p-nitrophenyl esters are all suitable reactive equivalents which may be successfully employed.

The preparation of a reactive intermediate represents a preferred process for the preparation of the compounds of this invention, and in particular, for the preparation of the cephalosporin derivatives herein described. Suitable coupling agents include carbonyldiimidazole, alkylchloroformate in which the alkyl group has from 1 to 5 carbon atoms, thionyl chloride, chloroacetonitrile, and bis-p-nitrophenyl carbonate. The preferred coupling agent is carbonyldiimidazole which, in general, is added to a solution of the 4-oxo-1-pyridinylacetic acid at a temperature below room temperature. The reaction mixture is permitted to reach room temperature and the reaction mixture subjected to reduced pressure in order to remove the carbon dioxide evolved during the formation of the imidazolide. The solution containing the reactive imidazolide intermediate is again chilled and now coupled with the appropriate $\beta$-lactam. Coupling is generally conducted at a temperature of from $0°$ C. to $150°$ C. for a period of 1-12 hours, whereupon the desired product is recovered using isolation techniques which are well known to those skilled in the art.

As an alternative to the direct coupling of the amino-$\beta$-lactam acid, the appropriate 6-aminopenicillanic acid or 7-aminocephalosporanic acid can be coupled as a neutral salt or in the form of an ester. Suitable salts include the trialkylammonium salts wherein the alkyl group has from 1 to 5 carbon atoms. Illustrative of such salts are those formed with trimethylamine or triethylamine. Esters represented by Formula (III) above are those in which the free carboxyl group of the amino-β-lactam has been suitably esterified. In those cases in which the ester group is subsequently removed in order to obtain the free acid, a preference is shown for those ester groups which are readily removed.

Both the silyl and stannyl esters are among those esters readily converted to the corresponding free acid under relatively mild conditions. Thus, for example, the esters may be subjected to hydrolysis, solvolysis or a nucleophilic exchange, without alteration of the remaining portion of the molecule. Suitable silylating agents include the alkyldisilazanes, as for example, tetramethyldisilazane and hexamethyldisilazane, or bis-trimethylsilylacetamide. Suitable stannylating agents include, for example, a bis-(tri-lower alkyl-tin)oxide such as bis-(tri-n-butyl-tin)oxide; a tri-lower alkyl-tin-hydroxide such as triethyl-tin-hydroxide; a tri-lower alkoxy-tin compound such as triethoxy-tin-hydroxide; and a tri-lower-alkyl-tin-halide such as tri-n-butyl-tin-chloride. The resulting silylated or stannylated carboxyl group can be regenerated to the desired free carboxylic acid by treatment with a neutral hydrogen-donating agent. Water or a lower alkanol, as for example, ethanol, is preferably used as the hydrogen-donating agent.

An alternative method for the preparation of the compounds of the present invention involves the treatment of a 6β-haloacetamidopenicillin or a 7β-haloacetamidocephalosporin derivative with a silylated 4-hydroxypyridine as illustrated in the following reaction scheme:

wherein $R_1$, $R_2$, $R_3$, $R_4$, $R_5$, $R_6$ and $R_8$ have the values previously assigned; $R_9$ is lower alkyl having from 1 to 5 carbon atoms; and Y is bromo or chloro.

The α-haloacetamido-β-lactam starting materials are known compounds which have been previously described in J. Med. Chem. 16, 1413 (1973), Belgium Patent 758,587, and U.S. Pat. Nos. 2,941,995 and 3,516,997. Preparation of the silylated 4-hydroxypyridines takes place with a suitable silylating agent as previously described. Suitable silylating agents include: diloweralkyl chlorosilane, triloweralkyl chlorosilane, diloweralkyl bromosilane and triloweralkyl bromosilane in which the loweralkyl group contains from 1 to 5 carbon atoms, tetramethyldisilazane, hexamethyldisilazane and bis-trimethylsilylacetamide.

The condensation reaction is generally conducted in an inert solvent such as chloroform, acetone, methylene chloride, dimethylformamide dioxane or acetonitrile. The temperature of the reaction can vary from −20° C. to 100° C. with a temperature of 20° C. preferred. Usually the reaction takes place in an inert atmosphere such as nitrogen, argon or helium. The reaction is generally conducted for a period of from 15 minutes to 36 hours, depending upon the nature of the reactants and the temperature at which the reaction is conducted. The reaction is usually complete in from 1 to 24 hours at the preferred temperature range.

In general, one equivalent of the silylated 4-hydroxypyridine derivative is reacted with one equivalent of the α-haloacetamido-β-lactam derivative. The β-lactam derivative can also be employed in the form of a salt, such as sodium, triethylamine, N,N-diethylaniline or diisopropylethylamine. Alternatively, the β-lactam may be in the form of an ester. Esters include those which can be readily removed to regenerate the free acid under mild conditions and which do not alter the

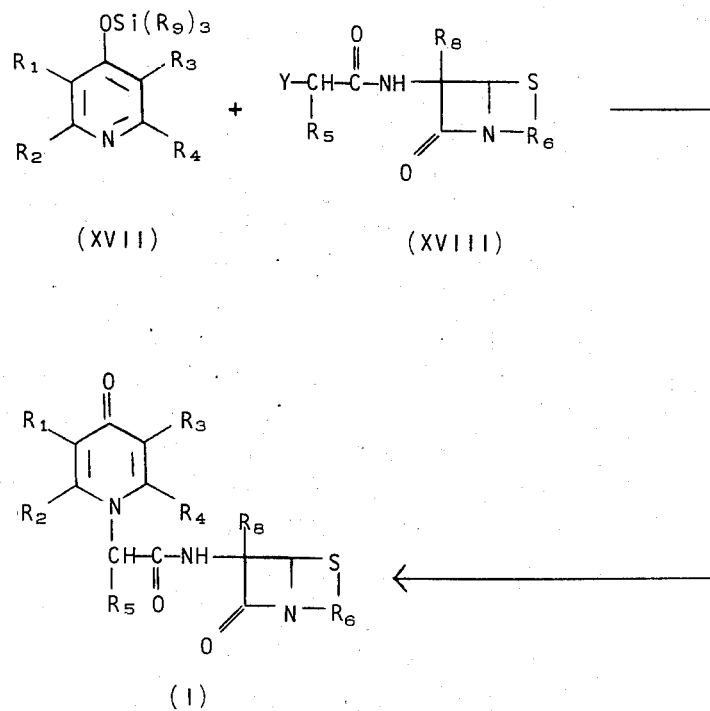

remainder of the molecule. Specifically, such esters include: t-butyl, trialkylsilyl and trialkylstannyl wherein the alkyl group has from 1 to 5 carbon atoms or benzyl esters, with the preferred esters being of the trialkylsilyl type. Such esters can be readily hydrolyzed to the free acid by treatment with a neutral hydrogen donating agent such as an alcohol.

In all of the aforementioned coupling reactions, compounds of the present invention having reactive functional groups which can interfere with the coupling reaction are protected using suitable blocking groups. Thus, carboxyl groups located on the 4-pyridone portion of the molecule or on the acetic acid portion of the molecule may be silylated or etherified with other labile esters as previously described. Similarly, amino and hydroxyl groups located on the 4-pyridone portion of the molecule can be suitably protected as labile derivatives. Such derivatives include silyl ethers, benzyl ethers and carbonate esters for hydroxyl groups, carbobenzyloxy, carbo-t-butyloxy and triphenylmethyl derivatives for amino groups.

An alternative route to the cephalosporin derivatives of Formula (I), wherein the symbol X represents 5-methyl-1,3,4-thiadiazol-2-ylthio or 1-methyl-1,2,3,4-tetrazol-5-ylthio, consists of the displacement of the acetoxy group from the methyl group at the 3-position of the substituted (4-oxo-1-pyridinylacetyl)aminocephalosporanic acids (XIX). This is illustrated in the following two reaction schemes:

wherein the symbols $R_1$, $R_2$, $R_3$, $R_4$, $R_5$ and $R_8$ have the values previously assigned.

The cephalosporanic acids of Formula (XIX) are dissolved with the 2-mercapto-5-methyl-1,3,4-thiadiazole (XX) or a metallic salt thereof in an inert solvent. Preferably an alkali metal salt of the cephalosporanic acid (XIX) is employed. These salts can be prepared, for example, by the treatment of the cephalosporanic acid with an alkali metal bicarbonate. The reaction is conducted in water or an aqueous organic solvent such as aqueous acetone, aqueous tetrahydrofuran or aqueous dimethylformamide. If desired, the pH of the reaction mixture can be controlled by the addition of aqueous buffers. If the free cephalosporanic acids are employed as starting materials, the reaction can be conducted in the presence of a base, such as sodium bicarbonate, triethylamine, or potassium bicarbonate.

The reaction can be conducted over a temperature range of from 25° C. to 110° C. Preferably a temperature range of from 50° C. to 100° C. is employed. If desired, the reaction may be conducted in the presence of an inert gas such as nitrogen or argon. The reaction time may vary from 15 minutes to 24 hours, with a reaction time of from 15 minutes to 6 hours preferably employed.

In certain instances the displacement of the acetoxy group from the methyl group at the 3-position results in the migration of the double bond to the 2-position of the β-lactam nucleus. Under those circumstances the

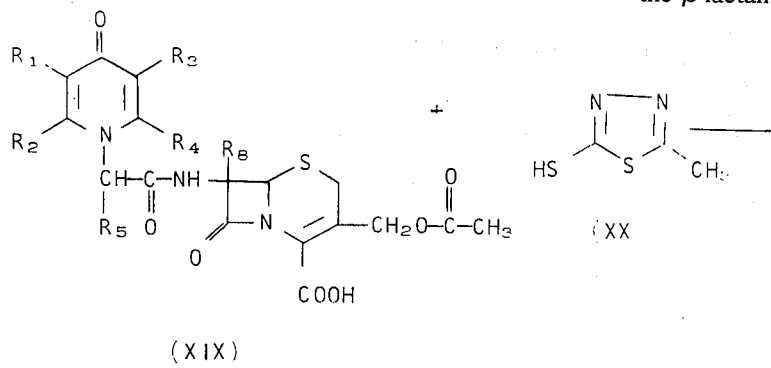

(XIX)

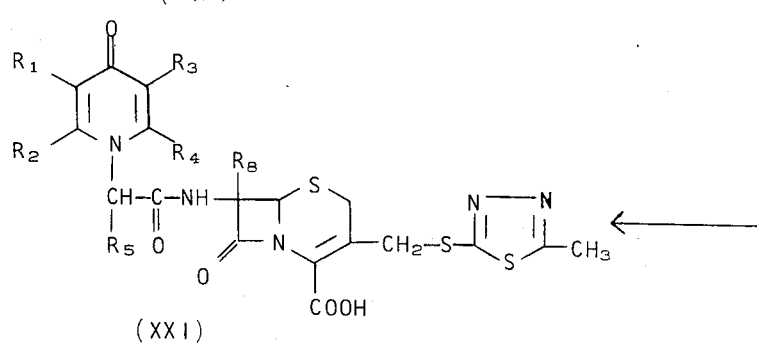

(XXI)

and (XIX) +

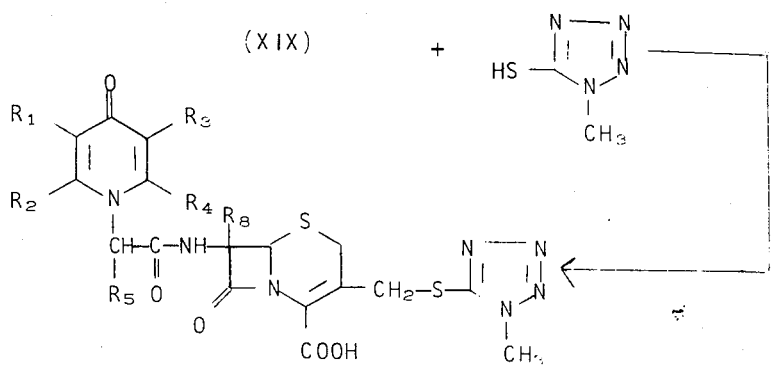

position of the double bond can be re-established by the oxidation of the ring sulfur to the sulfoxide with such oxidizing agents as hydrogen peroxide, sodium metaperiodate or an organic peracid. Subsequent reduction of the sulfoxide by means of catalytic hydogenation or sodium dithionite provides the desired cephalosporin derivatives which are unsaturated in the 3-position of the β-lactam nucleus.

The novel compounds of the present invention are biologically active and have been found to possess good antibacterial activity. Thus, they are useful antimicrobial agents having a broad-spectrum of antimicrobial activity in vitro against standard laboratory microorganisms which are used to screen activity against pathogenic bacteria. The antibacterial spectrum of typical compounds of the present invention is determined in a standard manner by the agar-dilution streakplate technique commonly used for the testing of new antibiotics.

The presence of the 7-methoxy substituent in the cephalosporin series has a beneficial effect in increasing or enchancing the spectrum of antimicrobial activity against certain gram-negative type microorganisms. More particularly, compounds containing the 7-methoxy substituent are active against certain gram-negative microorganisms that are resistant to compounds which do not contain the 7-methoxy substituent, as for example, *Enterobacter aerogenes*, *Enterobacter cloacae*, *Serratia marcescens* and the indole-positive species of Proteus.

The high in vitro antibacterial activity of the novel compounds of this invention not only makes them useful as pharmacological agents per se, but makes them useful as additives for animal feeds, as well as additives for materials which are subject to microbial deterioration. such as cutting oils and fuel oils. These compounds are also useful for their antibacterial effect in soaps, shampoos and in topical compositions for the treatment of wounds and burns.

The invention described herein is more particularly illustrated in conjunction with the following specific examples.

EXAMPLE 1

4-Pyridone-1-acetic acid

A suspension of 4-hydroxypyridine (19.0 g., 0.2 mole), triethylamine (22.2 g., 0.22 mole) and toluene (300 ml.) is heated to its reflux temperature and chlorotrimethylsilane (23 g., 0.2 mole) is added dropwise. The mixture is heated with stirring at its reflux temperature for 18 hours and filtered. The filtrate is evaporated and the residue is distilled at reduced pressure to yield 10.4 g. of silylated 4-hydroxypyridine, b.p.$_{15}$ 102°–104° C.

The silylated 4-hydroxypyridine (9 g., 0.054 mole) is mixed with ethylbromoacetate (25 ml.) and the mixture is stirred until the exothermic reaction subsides. The solidified mixture is triturated with ether and filtered. The solid is recrystallized from isopropyl alcohol to give 8 g. of 4-pyridone-1-acetic acid, ethyl ester, hydrobromide salt, having a m.p. of 195° C.

The ester, hydrobromide salt (8 g., 0.03 mole) prepared in this manner is added to a 1 N sodium hydroxide solution (80 ml) and the mixture is stirred for 5 hours, acidified and evaporated to 20 ml. The solution is chilled and filtered to yield 3.7 g of 4-pyridone-1-acetic acid having a m.p. 265°–6° C.

Following essentially the same procedure but substituting 3-methyl-4-pyridinol, 2,5-dimethyl-4-pyridinol, 3-nitro-4-pyridinol for the 4-hydroxypyridine above, there is obtained 3-methyl-4-pyridone-1-acetic acid, 2,5-dimethyl-4-pyridone-1-acetic acid and 3-nitro-4-pyridone-1-acetic acid, respectively.

EXAMPLE 2

4-Quinolone-1-acetic acid

4-Hydroxyquinoline trihydrate (20 g., 0.2 mole) is dissolved in a 50% aqueous potassium hydroxide solution and chloroacetic acid (20 g., 0.2 mole) is incrementally added. The resulting solution is heated at its reflux temperature for 18 hours, chilled, acidified and filtered to give 7 g of 4-quinolone-1-acetic acid having a m.p. 278°–279° C.

Following essentially the same procedure but substituting 3-cyano-2,6-dimethyl-4-pyridinol, 5-chloro-2-ethoxy-4-pyridinol or 3-trifluoromethyl-4-pyridinol for the 4-hydroxyquinoline trihydrate above, results in the preparation of 3-cyano-2,6-dimethyl-4-pyridone-1-acetic acid, 5-chloro-2-ethoxy-4-pyridone-1-acetic acid and 3-trifluoromethyl-4-pyridone-1-acetic acid, respectively.

EXAMPLE 3

2,6-Dimethyl-4-pyridone-1-acetic acid 2,6-Dimethyl-4-pyrone (12.4 g., 0.1 mole) is added to a solution of triethylamine (20 g., 0.2 mole) and glycine (7.5 g., 0.1 mole) in ethanol (100 ml)/water (10 ml). The mixture is heated to its reflux temperature for 4 days, chilled, acidified and filtered to yield 4 g of 2,6-dimethyl-4-pyridone-1-acetic acid, having a m.p. of 243° C.

Following essentially the same procedure but substituting 3-methoxy-2-methyl-4-pyrone, 3-hydroxy-4-pyrone, and 2,6-dicarbethoxy-4-pyrone for the 2,6-dimethyl-4-pyrone above, results in the formation of 3-methoxy-2-methyl-4-pyridone-1-acetic acid, 3-hydroxy-4-pyridone-1-acetic acid and 2,6-dicarbethoxy-4-pyridone-1-acetic acid, respectively.

EXAMPLE 4

7-[2-(4-Oxo-1-pyridinyl)acetylamino]-cephalosporanic acid, sodium salt

The compound 4-pyridone-1-acetic acid (3.06 g., 0.02 mole) is dissolved in dimethylformamide (50 ml) and the solution is chilled to 0° C. Carbonyldiimidazole (3.2 g., 0.02 mole) is added and the mixture is stirred under nitrogen at 0° C. for 30 minutes and then warmed to room temperature. The reaction flask is evacuated for 30 minutes to remove the carbon dioxide and chilled to −20° C. in a separate flask, 7-aminocephalosporanic acid is silylated by heating a suspension of 7-aminocephalosporanic acid (5.4 g., 0.02 mole) and hexamethyldisilazane (8 ml) in chloroform (50 ml) at reflux for 30 minutes. This solution is evaporated to dryness to remove the liberated ammonia. A solution of the residue in chloroform (50ml) is chilled to −20° C. and added to the imidazolide. The reaction mixture is stirred at 0° C. for 1 hour, warmed to room temperature and stirred overnight.

The solution is treated with 2 ml of methanol and the precipitated 7-aminocephalosporanic acid is removed by filtration. A solution of sodium 2-ethylhexanoate in n-butanol (10 ml of a 2 N solution) is added, and the mixture is diluted with ether to an approximate volume of 1 liter in order to precipitate the product. After reprecipitation from methanol with ether, a yield of 2.2 g. of 7-[2-(4-oxo-1-pyridinyl)acetylamino]cephalosporanic acid is obtained as a white solid having a m.p. of 180° C. (dec). Iodine titration indicated a purity of 72.7%.

Repeating essentially the same procedure but substituting 6-aminopenicillanic acid, 7-aminodesacetylcephalosporanic acid, 7-amino-3-[(5-methyl-1,3,4-thiadiazol-2-ylthio)methyl]decephalosporanic acid, 7-amino-3-[(1-methyl1,2,3,4-tetrazol-5-ylthio)methyl]decephalosporanic acid and 7-amino-7-methoxycephalosporanic acid for the 7-aminocephalosporanic acid above, results in the formation of the sodium salt of 6-[2-(4-oxo-1-pyridinyl)acetylamino]penicillanic acid, 7-[2-(4-oxo-1-pyridinyl)acetylamino]desacetylcephalosporanic acid, 7-[2-(4-oxo-1-pyridinyl)acetylamino]-3-[(5-methyl-1,3,4-thiadiazol-2-ylthio)methyl]decephalosporanic acid, 7-[2-(4-oxo-1-pyridinyl)acetylamino]-3-[(1-methyl-1,2,3,4-tetrazol-5-ylthio)methyl]decephalosporanic acid, and 7-methoxy-7-[2-(4-oxo-1-pyridinyl)acetylamino]cephalosporanic acid, respectively.

EXAMPLE 5

6-[2-(4-Oxo-1-quinolinyl)acetylamino]penicillanic acid, sodium salt

A solution of 4-quinolone-1-acetic acid (4.1 g., 0.02 mole) in 50 ml of dimethylformamide is placed under an atmosphere of nitrogen, chilled to 10° C. and carbonyldiimidazole (3.2 g., 0.02 mole) is added in one portion. After the mixture has warmed to room temperature the flask is evacuated for 15 minutes to remove the carbon dioxide evolved in formation of the imidazolide. The solution is chilled to 10° C. and a solution of 6-aminopenicillanic acid (4.4 g., 0.02 mole) and triethylamine (5 g., 20% excess) in chloroform (50 ml) is added. The reaction mixture is stirred at 10° C. for 1 hour, warmed to room temperature and stirring is continued for an additional 3 hours.

Ten ml of a 2 N solution of sodium 2-ethylhexanoate in butanol is added and the product is precipitated by the addition of ether (700 ml). The 6-[2-(4-oxo-1-quinolinyl)acetylamino]penicillanic acid is filtered, reprecipitated from methanol with ether and vacuum dried to yield 4.8 g of a white solid, m.p. 204° C. (dec). Iodine titration indicates 86.4% purity.

Repeating essentially the same procedure, but substituting 2,5-dimethyl-4-pyridone-1-acetic acid, 3-nitro-4-pyridone-1-acetic acid, 3-hydroxy-4-pyridone-1-acetic acid and 3,5-diiodo-4-pyridone-1-acetic acid for the 4-quinoline-1-acetic acid above, results in the preparation of the sodium salt of 6-[2-(2,5-dimethyl-4-oxo-1-pyridinyl)acetylamino]penicillanic acid, 6-[2-(3-nitro-4-oxo-1-pyridinyl)acetylamino]penicillanic acid, 6-[2-(3-hydroxy-4-oxo-1-pyridinyl)acetylamino]penicillanic acid and 6-[2-(3,5-diiodo-4-oxo-1-pyridinyl)acetylamino]penicillanic acid, respectively.

Substituting 7-amino-7-methoxycephalosporanic acid for the 6-amino penicillanic acid above results in the formation of the sodium salts of 6-[2-(4-oxo-1-quinolinyl)acetylamino]-7-methoxycephalosporanic acid,
6-[2-(2,5-dimethyl-4-oxo-1-pyridinyl)acetylamino]-7-methoxycephalosporanic acid,
6-[2-(3-nitro-4-oxo-1-pyridinyl)acetylamino]-7-methoxycephalosporanic acid,
6-[2-(3-hydroxy-4-oxo-1-pyridinyl)acetylamino]-7-methoxycephalosporanic acid, and
6-[2-(3,5-diiodo-4-oxo-1-pyridinyl)acetylamino]-7-methoxycephalosporanic acid.

EXAMPLE 6

7-[2-(2,6-Dimethyl-4-oxo-1-pyridinyl)acetylamino]-cephalosporanic acid, sodium salt 2,6-Dimethyl-4-pyridone-1-acetic acid (3.6 g., 0.02 mole) is dissolved in dimethylformamide (50 ml.) and the solution is chilled to 0° C. Carbonyldiimidazole (3.2 g., 0.02 mole) is added and the mixture is stirred under nitrogen at 0° C. for 30 minutes and permitted to warm to room temperature. The reaction flask is evacuated for 30 minutes to remove the evolved carbon dioxide. The resulting solution is chilled to −20° C. and a chloroform solution (50 ml.) of trimethylsilyl-7-aminocephalosporanic acid (0.02 mole) prepared as in Example 4 above, is added thereto. The reaction mixture is stirred at 0° C. for 1 hour, warmed to room temperature and stirred overnight.

The reaction mixture is treated with 2 ml. of methanol and the precipitated 7-aminocephalosporanic acid is removed by filtration. A 2 N solution of sodium 2-ethylhexanoate in n-butanol (10 ml.) is added to the reaction mixture, which is diluted to 1 liter with ether and filtered. The 7-[2-(2,6-dimethyl-4-oxo-1-pyridinyl)acetylamino]cephalosporanic acid so obtained is reprecipitated from methanol using ether and vacuum dried to yield 5.0 g. of a white powder having a m.p. of 240° C.

Following essentially the same procedure but substituting 3-methyl-4-pyridone-1-acetic acid, 5,6,7,8-tetrahydro-4-quinolone-1-acetic acid, 5-chloro-2-ethoxy-4-pyridone-1-acetic acid, 3-trifluoromethyl-4-pyridone-1-acetic acid and 3-hydroxy-4-pyridone-1-acetic acid for the 2,6-dimethyl-4-pyridone-1-acetic acid above results in the preparation of the sodium salts of 7-[2-(3-methyl-4-oxo-1-pyridinyl)acetylamino]cephalosporanic acid, 7-[2-(5,6,7,8-tetrahydro-4-oxo-1-quinolinyl)acetylamino]cephalosporanic acid, 7-[2-(5-chloro-2-ethoxy-4-oxo-1-pyridinyl)acetylamino]cephalosporanic acid, 7-[2-(3-trifluoromethyl-4-oxo-1-pyridinyl)acetylamino]cephalosporanic acid and 7-[2-(3-hydroxy-4-oxo-1-pyridinyl)acetylamino]cephalosporanic acid, respectively.

Substituting trimethylsilyl-6-amino-6-methoxypenicillanic acid for the trimethylsilyl-7-aminocephalosporanic acid above results in the formation of the sodium salts of 6-[2-(2,6-dimethyl-4-oxo-1-pyridinyl)acetylamino]-6-methoxypenicillanic acid,
6-[2-(3-methyl-4-oxo-1-pyridinyl)acetylamino]-6-methoxypenicillanic acid,
6-[2-(5,6,7,8-tetrahydro-4-oxo-1-quinolinyl)acetylamino]-6-methoxypenicillanic acid,
6-[2-(5-chloro-2-ethoxy-4-oxo-1-pyridinyl)acetylamino]-6-methoxypenicillanic acid,
6-[2-(3-trifluoromethyl-2-oxo-1-pyridinyl)acetylamino]-6-methoxypenicillanic acid, and
6-[2-(3-hydroxy-4-oxo-1-pyridinyl)acetylamino]-6-methoxypenicillanic acid.

EXAMPLE 7

7-[2-(4-Oxo-1-pyridinyl)acetylamino]-3-(pyridiniummethyl)decephalosporanic acid

7-[2-(4-Oxo-1-pyridinyl)acetylamino]cephalosporanic acid, sodium salt, is dissolved in water and reacted with pyridine in the presence of potassium thiocyanate at 60° C. for 6 hours. Work-up is conducted according to J. L. Spencer, et al., J. Org. Chem. 32, 500 (1967) and results in the preparation of 7-[2-(4-oxo-1-pyridinyl)acetylamino]-3-(pyridiniummethyl)decephalosporanic acid as the zwitterion.

EXAMPLE 8

7-[2-(4-Oxo-1-pyridinyl)acetylamino]desacetylcephalosporanic acid

7-[2-(4-Oxo-1-pyridinyl)acetylamino]cephalosporanic acid, sodium salt, is treated with an acetyl esterase isolated from orange peel according to J. D'A. Jeffery, et al., Biochem. J., 81, 591 (1961) to yield 7-[2-(4-oxo-1-pyridinyl)acetylamino]desacetylcephalosporanic acid, sodium salt.

EXAMPLE 9

4-Trimethylsilyloxypyridine

To 500 g. of crude 4-hydroxypyridine is added 5.5 l. of toluene. The mixture is heated with stirring and approximately 700 ml. of toluene is distilled in order to remove any water present. The reaction mixture is maintained at its reflux temperature and trimethylsilylchloride (543 g.) is slowly added thereto. The reaction mixture is refluxed for approximately 3 hours, cooled and filtered. The filtrate is evaporated under reduced pressure to remove the toluene and the residue distilled at 18–20 mm. yielding 620 g. of 4-trimethylsilyloxypyridine having a b.p. of 95°–6° C. at 18–20 mm.

EXAMPLE 10

7-[2-(4-Oxo-1-pyridinyl)acetylamino]cephalosporanic acid, sodium salt

To 20.0 g. of 7-(2-bromoacetamido)cephalosporanic acid, prepared in accordance with U.S. Pat. No. 3,647,789, is added 135 ml. of chloroform and 20 ml. of N,O-bis-(trimethylsilyl)acetamide. The mixture is stirred for about 1 hour under an atmosphere of dry nitrogen gas, 9.4 ml. of 4-trimethylsiloxypyridine added and the resulting mixture stirred at room temperature for approximately 15 hours while maintaining an atmosphere of dry nitrogen gas. Methyl alcohol (80 ml.) is added to the reaction mixture with stirring until all of the precipitate which initially forms is dissolved. The mixture is poured into approximately 1 liter of anhydrous ether with stirring, the solvent removed by decantation, and the sticky precipitate which remains is dissolved in an additional 400 ml. of methyl alcohol. A solution of 2 N sodium-2-ethylhexanoate (65 ml.) in n-butanol is added to the solution containing the dissolved precipitate, and the resulting mixture is treated with charcoal and filtered through a bed of diatomaceous earth. Isopropyl alcohol (900 ml.) is slowly added to the filtrate. The precipitate which forms is removed by filtration, washed with ether and dried in vacuo to yield 17.2 gms. of 7-[2-(4-oxo-1-pyridinyl)acetylamino]-cephalosporanic acid, sodium salt.

Following essentially the same procedure and substituting 7-[2-chloroacetamido]-7-methoxycephalosporanic acid, 7-[2-chloro-2-methylacetamido]desacetylcephalosporanic acid, 7-[2-bromo-2-carbethoxyacetamido]desacetoxycephalosporanic acid, 6-[2-chloro-2-methylacetamido]penicillanic acid, 6-[2-bromoacetamido]-6-methoxypenicillanic acid, and 6-[2-bromo-2-carbethoxyacetamido]penicillanic acid for the 7-(2-bromoacetamido)cephalosporanic acid above, results in the preparation of 7-[2-(4-oxo-1-pyridinyl)acetylamino]-7-methoxycephalosporanic acid, 7-[2-(4-oxo-1-pyridinyl)-2-methylacetylamino]desacetylcephalosporanic acid, 7-[2-(4-oxo-1-pyridinyl)-2-carbethoxyacetylamino]desacetoxycephalosporanic acid, 6-[2-(4-oxo-1-pyridinyl)-2-methylacetylamino]penicillanic acid, 6-[2-(4-oxo-1-pyridinyl)acetylamino]-6-methoxypenicillanic acid, and 6-[2-(4-oxo-1-pyridinyl)-2-carbethoxyacetylamino]penicillanic acid as their sodium salts, respectively.

Substituting 2,6-dimethyl-4-trimethylsilyloxypyridine, 2,6-bis(carbotrimethylsilyloxy)-4-trimethylsilyloxypyridine and 3-chloro-4-trimethylsilyloxypyridine for the 4-trimethylsiloxypyridine above results in the formation of the corresponding 2-(2,6-dimethyl-4-oxo-1-pyridinyl), 2-(2,6-dicarboxy-4-oxo-1-pyridinyl), and 2-(3-chloro-4-oxo-1-pyridinyl) derivatives of the various cephalosporanic and penicillanic acids shown as their sodium salts, respectively.

EXAMPLE 11

7-(α-Bromoacetylamino)-3-[(5-methyl-1,3,4-thiadiazol-2-ylthio)methyl]decephalosporanic acid To 1.4 g. of 7-amino-3-[(5-methyl-1,3,4-thiadiazol-2-ylthio)methyl]decephalosporanic acid, prepared as described in U.S. Pat. No. 3,516,997, and contained in a stirred mixture of 25 ml. of water and 25 ml. of acetone is added 3 g. of sodium bicarbonate. The mixture is chilled to −10° C. and 2.2 g. of bromoacetyl bromide in one ml. of acetone is slowly added to the stirred mixture over a period of 10 minutes. The mixture is stirred for an additional hour at −10° C. and permitted to come to room temperature. The reaction mixture is extracted with ethyl acetate and the organic phase is discarded. The aqueous phase is layered with 100 ml. of ethyl acetate and the aqueous phase adjusted to a pH of 2 with a 40% solution of phosphoric acid. The organic phase is separated, dried over sodium sulfate and decolorized with charcoal. The solution is filtered, evaporated and the residue is triturated with ether. The residue is dried in vacuo to yield 0.7 g. of 7-(α-bromoacetylamino)-3-[(5-methyl-1,3,4-thiadiazol-2-ylthio)methyl]decephalosporanic acid.

Following essentially the same procedure and substituting 7-amino-7-methoxy-3-[(5-methyl-1,3,4-thiadiazol-2-ylthio)methyl]decephalosporanic acid, 7-amino-3-[(1-methyl-1,2,3,4-tetrazol-5-ylthio)methyl]decephalosporanic acid and 7-amino-7-methoxy-3-[(1-methyl-1,2,3,4-tetrazol-5-ylthio)methyl]decephalosporanic acid for the 7-amino-3-[(5-methyl-1,3,4-thiadiazol-2-ylthio)methyl]decephalosporanic acid above results in the formation of 7-(α-bromoacetylamino)-7-methoxy-3-[(5-methyl-1,3,4-thiadiazol-2-ylthio)methyl]decephalosporanic acid, 7-(α-bromoacetylamino)-3-[(1-methyl-1,2,3,4-tetrazol-5-ylthio)methyl]decephalosporanic acid, and 7-(α-bromoacetylamino)-7-methoxy-3-[(1-methyl-1,2,3,4-tetrazol-5-ylthio)methyl]decephalosporanic acid, respectively.

EXAMPLE 12

7-[2-(4-Oxo-1-pyridinyl)acetylamino]-3-[(5-methyl-1,3,4-thiadiazol-2-ylthio)methyl]decephalosporanic acid, sodium salt To 4.65 g. of 7-(α-bromoacetylamino)-3-[(5-methyl-1,3,4-thiadiazol-2-ylthio)methyl]decephalosporanic, as prepared in Example 11, is added 50 ml. of chloroform and 5 ml. of N,O-bis(trimethylsilyl)acetamide. The mixture is stirred under an atmosphere of nitrogen until a clear solution is obtained, 4-trimethylsilyloxypyridine (1.6 g.) is added and the mixture stirred for 18 hours under nitrogen. Methyl alcohol (5 ml.) is added and the solid precipitate which forms is collected via filtration. The precipitate is dissolved in 100 ml. of methyl alcohol, 5 ml. of a 2 N sodium 2-ethylhexanoate solution in n-butanol is added, followed by 200 ml. of ether. The precipitate which forms is collected via filtration and dried under vacuum to yield the sodium salt of 7-[2-(4-oxo-1-pyridinyl)acetylamino]-3-[(5-methyl-1,3,4-thiadiazol-2-ylthio)methyl]decephalosporanic acid.

Following essentially the same procedure but substituting 7-(α-bromoacetylamino)-7-methoxy-3-[(5-methyl-1,3,4-thiadiazol-2-ylthio)methyl]decephalosporanic acid, 7-(α-bromoacetylamino)-3-[(1-methyl-1,2,3,4-tetrazol-5-ylthio)methyl]decephalosporanic acid or 7-(α-bromoacetylamino)-7-methoxy-3-[(1-methyl-1,2,3,4-tetrazol-5-ylthio)methyl]decephalosporanic acid for the 7-(α-bromoacetylamino)-3-[(5-methyl-1,3,4-thiadiazol-2-ylthio)methyl]decephalosporanic acid above results in the formation of the sodium salts of 7-methoxy-7-[2-(4-oxo-1-pyridinyl)acetylamino]-3-[(5-methyl-1,3,4-thiadiazol-2-ylthio)methyl]decephalosporanic acid, 7-[2-(4-oxo-1-pyridinyl)acetylamino]-3-[(1-methyl-1,2,3,4-tetrazol-2-ylthio)methyl]decephalosporanic acid, and 7-methoxy-7-[2-(4-oxo-1-pyridinyl)acetylamino]-3-[(1-methyl-1,2,3,4-tetrazol-2-ylthio)methyl]decephalosporanic acid, respectively.

EXAMPLE 13

7-[2-(3-cyano-4-oxo-1-pyridinyl)acetylamino]-3-[(5-methyl-1,3,4-thiadiazol-2-ylthio)methyl]decephalosporanic acid, sodium salt To a chloroform solution of 7-(α-bromoacetylamino)-3-[(5-methyl-1,3,4-thiadiazol-2-ylthio)methyl]decephalosporanic acid and N,N-diethylaniline is added one equivalent of 3-cyano-4-trimethylsilyloxypyridine. The mixture is stirred for approximately 15 hours at room temperature under an atmosphere of nitrogen. Methyl alcohol is added followed by the addition of anhydrous ether. The precipitate which forms is removed by filtration, dissolved in methyl alcohol and an equivalent amount of a solution of 2-N-sodium 2-ethylhexanoate in butanol added thereto. An equal volume of ether is added and the precipitate which forms is removed by filtration and dried under vacuum to yield 7-[2-(3-cyano-4-oxo-1-pyridinyl)acetylamino]-3-[(5-methyl-1,3,4-thiadiazol-2-ylthio)methyl]decephalosporanic acid as the sodium salt.

EXAMPLE 14

7-Methoxy-7-[2-(4-oxo-1-quinolinyl)acetylamino]-3-[(1-methyl-1,2,3,4-tetrazol-5-ylthio)methyl]decephalosporanic acid, sodium salt A mixture of sodium 7-methoxy-7-[2-(4-oxo-1-quinolinyl)acetylamino]cephalosporanate (3.5 g.), sodium bicarbonate (2.5 g.), 1-methyl-5-mercapto-1,2,3,4-tetrazol (2.6 g.), and 60 ml. of water is heated at about 70° C. under an atmosphere of nitrogen for about 4 hours. The reaction mixture is cooled and evaporated under reduced pressure. The residue which remains is triturated with acetone, dissolved in methanol and filtered. Isopropyl alcohol is added to the filtrate to form a precipitate, which is collected by filtration and vacuum dried to yield a precipitate of 7-methoxy-7-[2-(4-oxo-1-quinolinyl)acetylamino]-3-[(1-methyl-1,2,3,4-tetrazol-5-ylthio)methyl]decephalosporanic acid as the sodium salt.

Following essentially the same procedure but substituting 7-[2-(4-oxo-1-pyridinyl)acetylamino]cephalosporanic acid or 7-[2-methyl-2-(2,6-dimethyl-4-oxo-1-pyridinyl)acetylamino]cephalosporanic acid results in the formation of 7-[2-(4-oxo-1-pyridinyl)acetylamino]-3-[(1-methyl-1,2,3,4-tetrazol-5-ylthio)methyl]decephalosporanic acid and 7-[2-methyl-2-(2,6-dimethyl-4-oxo-1-pyridinyl)acetylamino]-3-[(1-methyl-1,2,3,4-tetrazol-5-ylthio)methyl]decephalosporanic acid as their sodium salts, respectively.

EXAMPLE 15

7-[2-(4-oxo-1-pyridinyl)acetylamino]-3-[(5-methyl-1,3,4-thiadiazol-2-ylthio)methyl]decephalosporanic acid, sodium salt To a solution of (5 g.) of sodium 7-[2-(4-oxo-1-pyridinyl)acetylamino]cephalosporanate in 500 ml. of water is added (0.95 g.) of sodium bicarbonate and (2.96 g.) of 2-mercapto-5-methyl-1,3,4-thiadiazole. The mixture is heated under a nitrogen atmosphere at 70° C. for 3 hours and evaporated under reduced pressure. The residue is dissolved in 50 ml. of methanol and treated with an excess of acetonitrile. The white precipitate which forms is removed by filtration, washed with acetonitrile and dried under vacuum to yield (4.3 g.) 7-[2-(4-oxo-1-pyridinyl)acetylamino]-3-[(5-methyl-1,3,4-thiadiazol-2-ylthio)methyl]decephalosporanic acid as the sodium salt.

Following essentially the same procedure but substituting the sodium salts of 7-methoxy-7-[2-(4-oxo-1-quinolinyl)acetylamino]cephalosporanic acid, 7-methoxy-7-[2-(4-oxo-1-pyridinyl)acetylamino]cephalosporanic acid or 7-[2-methyl-2-(2,6-dimethyl-4-oxo-1-pyridinyl)acetylamino]cephalosporanic acid results in the formation of 7-methoxy-7-[2-(4-oxo-1-quinolinyl)acetylamino]-3-[(5-methyl-1,3,4-thiadiazol-2-ylthio)methyl]decephalosporanic acid, 7-methoxy-7-[2-(4-oxo-1-pyridinyl)acetylamino]-3-[(5-methyl-1,3,4-thiadiazol-2-ylthio)methyl]decephalosporanic acid or 7-[2-methyl-2-(2,6-dimethyl-4-oxo-1-pyridinyl)acetylamino]-3-[(5-methyl-1,3,4-thiadiazol-2-ylthio)methyl]decephalosporanic acid as their sodium salts, respectively.

EXAMPLE 16

Pivaloyloxymethyl 7-[2-(4-oxo-1-pyridinyl)acetylamino]cephalosporanate

To (4.5 g.) of sodium 7-[2-(4-oxo-1-pyridinyl)acetylamino]cephalosporanate dissolved in 40 ml. of dimethylformamide and chilled to 0° C. is added (2.6 g.) of pivaloyloxymethyliodide and the solution stirred for approximately 25 minutes. The mixture is diluted with ethyl acetate (170 ml.), washed well with water and then washed with a dilute solution of sodium bicarbonate. The organic phase is dried over anhydrous sodium sulfate, filtered and evaporated to dryness to yield pivaloyloxymethyl 7-[2-(4-oxo-1-pyridinyl)acetylamino]cephalosporanate.

Following essentially the same procedure but substituting acetoxymethyliodide, N-chloromethyl-N-methylurethane, or p-acetoxybenzylbromide for the pivaloyloxymethyliodide above results in the formation of acetoxymethyl 7-[2-(4-oxo-1-pyridinyl)acetylamino]cephalosporanate, N-ethoxycarbonyl-N-methylaminomethyl 7-[2-(4-oxo-1-pyridinyl)acetylamino]cephalosporanate and p-acetyloxybenzyl 7-[2-(4-oxo-1-pyridinyl)acetylamino]cephalosporanate, respectively.

Substituting the sodium salts of 7-methoxy-7-[2-(4-oxo-1-pyridinyl)acetylamino]-3-[(1-methyl-1,2,3,4-tetrazol-5-ylthio)methyl]decephalosporanic acid, 6-methoxy-6-[2-(3-cyano-4-oxo-1-pyridinyl)acetylamino]penicillanic acid or 6-[2-(4-oxo-1-quinolinyl)-2-methylacetylamino]penicillanic acid for the 7-[2-(4-oxo-1-pyridinyl)acetylamino]cephalosporanic acid above results in the formation of pivaloyloxymethyl 7-methoxy-7-[2-(4-oxo-1-pyridinyl)acetylamino]-3-[(1-methyl-1,2,3,4-tetrazol-5-ylthio)methyl]decephalosporanate, pivaloyloxymethyl 6-methoxy-6-[2-(3-cyano-4-oxo-1-pyridinyl)acetylamino]penicillanate and pivaloyloxymethyl 6-[2-(4-oxo-1-quinolinyl)-2-methylacetylamino]penicillanate, respectively.

EXAMPLE 17

N-Ethoxycarbonyl-N-methylaminomethyl 7-[2-(4-oxo-1-pyridinyl)acetylamino]-3-[(5-methyl-1,3,4-thiadiazol-2-ylthio)methyl]decephalosporanate To a slurry of sodium 7-[2-(4-oxo-1-pyridinyl)acetylamino]-3-[(5-methyl-1,3,4-thiadiazol-2-ylthio)methyl]decephalosporanate (0.01 mole) contained in 20 ml. of dimethylformamide and maintained at a temperature of 0°–5° C. is added a solution of N-chloromethyl-N-methylurethane (0.01 mole) contained in 5 ml. of dimethylformamide. The mixture is stirred for about one hour and poured into water. The precipitate which forms is dissolved in ethyl acetate, washed with water followed by a dilute solution of sodium bicarbonate and dried over magnesium sulfate. The solution is evaporated under reduced pressure to yield the desired N-ethoxycarbonyl-N-methylaminomethyl 7-[2-(4-oxo-1-pyridinyl)acetylamino]-3-[(5-methyl-1,3,4-thiadiazol-2-ylthio)methyl]decephalosporanate.

EXAMPLE 18

Specific nutrient agar plates are completely innoculated with the various test organisms. Filter paper discs are placed on the surface of the agar and wetted with 0.1 ml. of a solution containing 10, 100 and 1,000 micrograms of the test compound. Zones of inhibition of microbial growth are used to indicate the antibacterial activity of the test compound against the various test organisms employed.

The following table summarizes the in vitro activity of the following representative compounds: 6-[2-(4-oxo-1-pyridinyl)acetylamino]penicillanic acid, sodium salt (1), 7-[2-(4-oxo-1-pyridinyl)acetylamino]-desacetoxycephalosporanic acid (2), 6-[2-(3,5-diiodo-4-oxo-1-pyridinyl)acetylamino]penicillanic acid, sodium salt (3), 7-[2-(2,6-dimethyl-4-oxo-1-pyridinyl)acetylamino]desacetoxycephalosporanic acid, sodium salt (4), 7-[2-(4-oxo-1-pyridinyl)acetylamino]cephalosporanic acid, sodium salt (5) and 6-[2-(4-oxo-1-quinolinyl)acetylamino]penicillanic acid, sodium salt (6).

| | MINIMAL INHIBITING CONCENTRATION (mcg/ml) | | | | |
|---|---|---|---|---|---|
| Compound | Staphylococcus aureus | Salmonella schottmuelleri | Streptococcus pyogenes | (Penicillinase Producing) Staphylococcus aureus | Acid Resistance |
| (1) | 10 | 100 | 1,000 | 1,000 | Yes |
| (2) | 1,000 | >1,000 | 1,000 | >1,000 | Yes |
| (3) | 10 | 100 | >1,000 | >1,000 | Yes |
| (4) | 1,000 | >1,000 | >1,000 | >1,000 | Yes |
| (5) | 10 | 100 | 100 | 1,000 | Yes |
| (6) | 10 | 100 | 1,000 | 1,000 | Yes |

We claim:
1. A 6-[(4-oxo-1-pyridinyl)acetylamino]penicillin derivative having the formula:

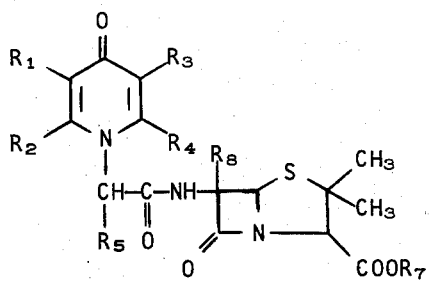

wherein
$R_1$, $R_2$, $R_3$ and $R_4$ are each selected from the group consisting of hydrogen, halogen, loweralkyl having from 1 to 4 carbon atoms, trifluoromethyl, carboxy, carbomethoxy, carbethoxy and when $R_1$ is taken in combination with $R_2$ forms the cyclic radical $-CH_2CH_2CH_2CH_2-$ and $-CH=CH-CH=CH-$;

$R_5$ is selected from the group consisting of hydrogen, methyl, carboxy, carbomethoxy and carbethoxy;

$R_7$ is selected from the group consisting of hydrogen, alkanoyloxymethyl, alkanoylaminomethyl, alkoxycarbonylaminomethyl and p-(alkanoyloxy)benzyl in which the alkanoyl or alkoxy group contains from 1 to 5 carbon atoms;

$R_8$ is hydrogen or methoxy; and
the pharmaceutically acceptable salts thereof.

2. A compound according to claim 1, wherein $R_8$ is hydrogen.

3. A compound according to claim 1, wherein $R_8$ is methoxy.

4. A compound according to claim 1, wherein $R_5$ is hydrogen.

5. A compound of claim 1 which is 6-[2-(4-oxo-1-pyridinyl)acetylamino]penicillanic acid and the pharmaceutically acceptable salts thereof.

6. A compound of claim 1 which is 6-[2-(3,5-diiodo-4-oxo-1-pyridinyl)acetylamino]penicillanic acid and the pharmaceutically acceptable salts thereof.

* * * * *